United States Patent
Shafir et al.

(10) Patent No.: US 10,054,423 B2
(45) Date of Patent: Aug. 21, 2018

(54) OPTICAL METHOD AND SYSTEM FOR CRITICAL DIMENSIONS AND THICKNESS CHARACTERIZATION

(71) Applicant: NOVA MEASURING INSTRUMENTS LTD., Rehovot (IL)

(72) Inventors: Dror Shafir, Kiryat Ono (IL); Gilad Barak, Rehovot (IL); Shay Wolfling, Kiryat Ono (IL)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 0 days.

(21) Appl. No.: 14/655,791

(22) PCT Filed: Dec. 26, 2013

(86) PCT No.: PCT/IL2013/051075
§ 371 (c)(1),
(2) Date: Jun. 26, 2015

(87) PCT Pub. No.: WO2014/102792
PCT Pub. Date: Jul. 3, 2014

(65) Prior Publication Data
US 2015/0345934 A1 Dec. 3, 2015

Related U.S. Application Data

(60) Provisional application No. 61/746,236, filed on Dec. 27, 2012.

(51) Int. Cl.
*G01B 11/02* (2006.01)
*G01N 21/47* (2006.01)
(Continued)

(52) U.S. Cl.
CPC ......... *G01B 11/02* (2013.01); *G01N 21/4738* (2013.01); *G01N 21/956* (2013.01);
(Continued)

(58) Field of Classification Search
CPC ..................................................... G01B 11/02
(Continued)

(56) References Cited

U.S. PATENT DOCUMENTS 6,512,578 B1 * 1/2003 Komatsu ............ G01N 21/9501
250/559.37
8,289,515 B2 10/2012 Cohen et al.
(Continued)

OTHER PUBLICATIONS

Marathe et.al, "Coherent diffraction surface imaging in reflection geometry" Optics Express, 18 (7) 7253-7262 (Mar. 2010).
(Continued)

*Primary Examiner* — Tarifur Chowdhury
*Assistant Examiner* — Omar Nixon
(74) *Attorney, Agent, or Firm* — Browdy and Neimark, PLLC

(57) ABSTRACT

Method and system for measuring one or more parameters of a patterned structure, using light source producing an input beam of at least partially coherent light in spatial and temporal domains, a detection system comprising a position sensitive detector for receiving light and generating measured data indicative thereof, an optical system configured for focusing the input light beam onto a diffraction limited spot on a sample's surface, collecting an output light returned from the illuminated spot, and imaging the collected output light onto a light sensitive surface of the position sensitive detector, where an image being indicative of coherent summation of output light portions propagating from the structure in different directions.

15 Claims, 3 Drawing Sheets

(51) Int. Cl.
*G01N 21/956* (2006.01)
*G02B 21/36* (2006.01)
(52) U.S. Cl.
CPC .................. *G01B 2210/56* (2013.01); *G01N 2201/06113* (2013.01); *G01N 2201/12* (2013.01); *G02B 21/365* (2013.01)
(58) Field of Classification Search
USPC ........................................................ 356/364
See application file for complete search history.

(56) References Cited

U.S. PATENT DOCUMENTS

| | | | |
|---|---|---|---|
| 2004/0238636 A1* | 12/2004 | Marx | G01B 11/02 235/454 |
| 2005/0068540 A1* | 3/2005 | De Groot | G01B 11/0675 356/512 |
| 2005/0231737 A1* | 10/2005 | Chu | G03F 7/70625 356/636 |
| 2007/0252986 A1 | 11/2007 | Sandstrom | |
| 2008/0015802 A1* | 1/2008 | Urano | G01N 21/4738 702/81 |
| 2008/0029913 A1* | 2/2008 | Taylor | G03F 7/70633 257/797 |
| 2009/0073563 A1 | 3/2009 | Betzig | |
| 2009/0174935 A1* | 7/2009 | Szulczewski | G02B 21/002 359/368 |
| 2009/0290156 A1 | 11/2009 | Popescu et al. | |
| 2010/0155609 A1* | 6/2010 | Silva | G01S 7/00 250/363.06 |
| 2010/0284027 A1* | 11/2010 | Scheiner | G01B 11/22 356/626 |
| 2011/0007314 A1 | 1/2011 | Den Boef et al. | |
| 2011/0069379 A1* | 3/2011 | Becker | G02B 21/248 359/368 |
| 2011/0235038 A1* | 9/2011 | Fukazawa | G01N 21/21 356/369 |
| 2012/0229891 A1* | 9/2012 | Liu | G01N 21/553 359/355 |
| 2012/0268717 A1* | 10/2012 | Zhou | A61B 3/1015 351/221 |
| 2012/0327503 A1* | 12/2012 | Manassen | G01J 1/4257 359/291 |
| 2013/0182263 A1* | 7/2013 | Shchegrov | G01B 9/02 356/512 |
| 2013/0282343 A1 | 10/2013 | Brill et al. | |
| 2013/0308131 A1 | 11/2013 | Barak et al. | |

OTHER PUBLICATIONS

International Search Report, dated May 15, 2014 issued in the corresponding application No. 2013/051075.

* cited by examiner

OPTICAL METHOD AND SYSTEM FOR CRITICAL DIMENSIONS AND THICKNESS CHARACTERIZATION

TECHNOLOGICAL FIELD AND BACKGROUND

As semiconductor technology progresses, shrinking device dimensions has become an increasingly complex task. Complementing metrology tools, allowing similar improvements in measurement capabilities, are critical for the continual process of this development. Commonly, optical metrology is applied to test structures comprised of a repeating array of identical elements. Optical metrology can acquire highly accurate and precise information on the geometry and material properties characterizing these structures, and thus provide the required information for better process and process control.

Several physical quantities are commonly measured by optical metrology. For example, optical reflectometry measures the reflection intensity for a broad spectrum, over a single (or small set) of incidence directions and different polarizations. Ellipsometry allows, in addition, access to information on the relative phase between different polarization states. Dome scatterometry measures the sample reflectivity over a large range of incidence directions, for a small set of wavelengths. In addition, different interferometry techniques are used to measure the phases of the scattered optical components. These could be the spectral components or the angular ones.

Various metrology techniques have been developed allowing measurements of the parameters of complex structure (three-dimensional structure) such as semiconductor wafers. Examples of such techniques are described in US 2013/308131, U.S. Pat. No. 8,289,515, US 2013/282343, all assigned to the assignee of the present application.

GENERAL DESCRIPTION

There is a need in the art for a novel approach for optical measurements of various parameters of patterned structures, such as critical dimensions and thickness characterization, as well as via profile, and optical properties of various layers in the structure.

As indicated above, as device dimensions shrink and sensitivity to process details becomes increasingly crucial, the ability to access more diverse and independent physical properties of the sample becomes of paramount importance. The optical scattering properties of a sample are derived from its geometrical and material characteristics, and as such allow highly effective means of gaining information on the sample. These can be measured by existing techniques such as reflectometry and ellipsometry which are used to access different aspects of the sample scattering properties. However, the entire set of scattering properties is currently not addressable using a single metrology technique.

The present invention provides a novel optical metrology technique, which allows convenient measurement of such properties of a sample which are not easily measured otherwise. These properties can be used, among other, for improving semiconductor manufacturing process and process control.

The technique of the present invention is termed here "Coherent Point Microscopy" (CPM). As will described below, the CPM technique of the invention provides for measuring a light intensity pattern from a sample related to the Fourier transform of the scattering matrix of a sample and thus containing information on both its amplitude and phase.

In some embodiments of the present invention, a CPM system is based on the use of so-called "critical illumination" when a point-like source is directly imaged onto the sample, or alternatively a collimated laser beam is focused on the sample or another illumination(s) having properties or characteristics of "critical illumination". Such illumination provides a range of illumination angles onto the sample and coherent interference between different illumination angles. Thus, the CPM approach utilizes a combination of an imaging optics in conjunction with coherent light source in critical illumination.

The technique of the present invention involves illumination of a diffraction limited spot on a sample, imaging such a point-like light source scattered from the sample onto a pixel matrix and using the image data to characterize the sample. This approach is based on the inventors' understanding of the following: In case the sample's surface responds to illumination like a so-called "perfect mirror", i.e. reflection by the sample does not depend on an incident angle and does not change polarization, the image on the detector is that image of the diffraction-limited light spot of the imaging optics, and presents the system 'point spread function' (PSF). However, for a nontrivial sample (practical sample), an image on the detector is formed by a reflected/scattering pattern which is directly related to the scattering matrix of the sample. Such image is significantly different from the diffraction-limited spot. The invention utilizes this change in the spot image for determining the sample's characteristics. More specifically, data indicative of the light response of the sample is analyzed to obtain applicative information about the sample's parameter(s) from the PSF of the system.

It should be noted that a CPM measurement is not primarily intended to be used as means for microscopy analysis of the sample. Whereas a microscopic image of the sample provides position-dependent information on the local reflectivity of the sample, a CPM image provides a highly nontrivial synthesis of the spatial and angular scattering properties.

The CPM technique of the present invention is based on pristine imaging capabilities for high-coherence light source. In this connection, it should be noted that commonly the use of coherent light introduces strong fringe and speckle effects which deteriorate the measurements, such that various technique are needed to reduce these effects based on the destruction of spatial coherence (e.g. Rotating diffusers). On the contrary, CPM utilizes spatial coherence of light, and the known techniques for destruction of spatial coherence would significantly deteriorate the CPM measurement. Generally, some minor spatial incoherence can be used in CPM measurements, as long as the imaging constraints between light-source and sample are kept.

It should be understood that in the CPM of the present invention, the spatial coherence of the light source allows different scattered angles to interfere on the detector and to create an interference pattern from which the information about the sample can be obtained. Critically illuminating a sample with coherent light creates a diffraction limited spot on the sample which is the smallest illumination configuration optically possible (i.e. is the optical resolution of the system). In the semiconductor manufacturing field, wafer real-estate is expensive and the ability to achieve metrological measurements on small test sites or even inside the functional areas (dies) is of significant benefit.

As indicated above, the CPM technique of the present invention provides information on the absolute value of the Fourier transform of a scattering matrix of the sample. Quite generally, all the scattering properties of a sample can be characterized by a physical property called "scattering matrix". The scattering matrix M provides the complex amplitude for scattering of any incident wave to any outgoing wave. An incident wave is typically characterized by a wavelength $\lambda_{in}$, a direction of propagation (an incidence direction) $\vec{\Omega}_{in}$ and a polarization state $\vec{P}_{in}$. An outgoing wave is similarly characterized by a wavelength $\lambda_{out}$, a direction of propagation (an outgoing direction) $\vec{\Omega}_{out}$ and a polarization state $\vec{P}_{out}$. For all optically linear samples (samples that do not show nonlinear optical effects), $\lambda_{in}=\lambda_{out}$, and accordingly the description below is focused on such cases, which is relevant for the majority of cases in the semiconductor industry.

As indicated above, the scattering matrix holds a complex quantity, allowing the outgoing and incident waves to have a phase difference. Consequently, it is convenient to use the following relation:

$$M_\lambda(\vec{\Omega}_{in},\vec{P}_{in},\vec{\Omega}_{out},\vec{P}_{out})=Ae^{i\phi}. \quad (1)$$

If a plane wave with wavelength $\lambda$ and polarization $\vec{P}_{in}$ impinges onto a sample with incidence direction $\vec{\Omega}_{in}$, the measured outgoing field at direction $\vec{\Omega}_{out}$ and polarization $\vec{P}_{out}$, has an amplitude A, and phase $\phi$ with respect to the incident wave.

The scattering matrix itself holds complex values, and accordingly the measured information does not fully specify both its amplitude and phase, but provides a mathematical relation between them, while the CPM setup provides for measuring the Fourier transform of the scattering matrix and thus provides a nontrivial combination of the amplitude and phase.

A Dome scatterometer, for example, can provide direct measurement of the amplitude A over various values of incident and outgoing directions and polarizations, for a set of wavelengths. Using the principles of the present invention, as will be described in details below, one can gain information on both the amplitude A and phase $\phi$ for multiple incidence and outgoing directions. Moreover, in some embodiments of the present invention, one can measure both amplitude and phase, gaining substantial information content on the measured target.

Thus, according to a broad aspect of the invention, there is provided a measurement system for measuring one or more parameters of a patterned structure. The measurement system comprises: a light source system; a detection system comprising a position sensitive detector; and an optical system. The light source system is configured for producing an input beam of at least partially coherent light in spatial and temporal domains. The optical system is configured for focusing the input light beam onto a diffraction limited spot on a sample's surface, collecting an output light returned from the illuminated spot, and imaging the collected output light onto the light sensitive surface of the position sensitive detector. The image is indicative of coherent summation of output light portions propagating from the structure in different directions. Further provided in the system is a control unit configured for communication with the position sensitive detector for receiving data corresponding to the measured data indicative of an image of the collected output light, and processing the received measured data for determining a scattering matrix of the structure under measurements, and utilizing data indicative of the scattering matrix for determining the one or more parameters of the sample.

The measured image data corresponds to a reflection pattern of the structure defined by angular distribution of amplitude and phase of the output light. The control unit may be configured for utilizing one or more predetermined models for finding a combination of theoretical parameters of a patterned structure producing best fit between the measured data and data calculated by the one or more models, to thereby determine the one or more parameters of the structure. The control unit may be configured for determining a relation between the data indicative of the measured scattering matrix and known data about a point spread function (PSF) of the measurement system, such relation being indicative of a reflection pattern of the structure characterizing the one or more parameters of the structure.

Generally, with the technique of the present invention obtaining a single CPM image may be sufficient for determination of one or more parameters of the structure, e.g. critical dimensions of the pattern. In order to optimize the phase extraction, phase retrieval algorithms may be used, and/or through focus scanning during measurements, and/or the use of hybrid measurements, by utilizing additional light propagation (imaging) scheme and a corresponding detection mode, such as Dome scatterometry.

In some embodiments, the optical system comprises a polarization assembly including a polarizer in an optical path of the input light beam propagating towards the sample, and an analyzer in an optical path of the output light beam propagating from the sample to the detector.

The optical system may be configured for normal and/or oblique incidence operational mode

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
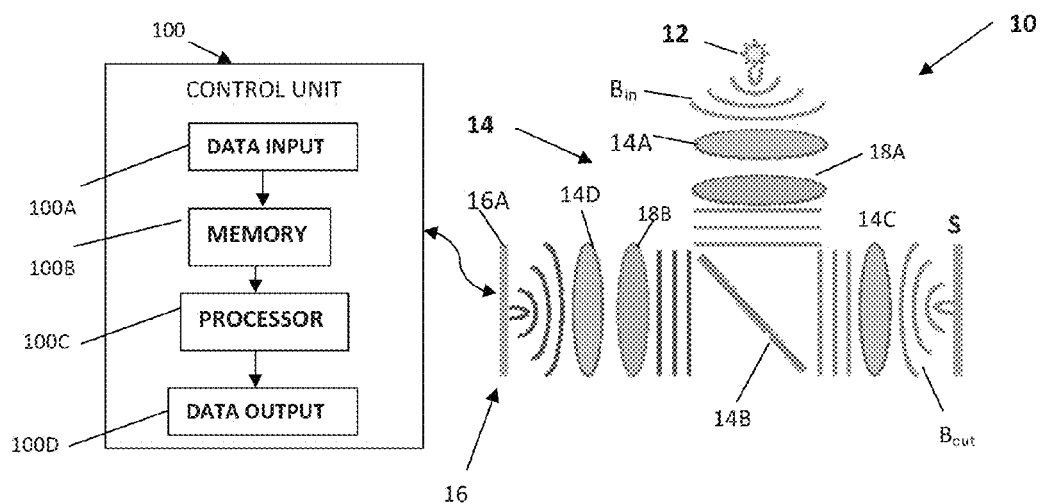
FIG. 1 schematically illustrates an example of a CPM system of the present invention.

Reference is made to FIG. 1 exemplifying a measurement system 10 of the present invention configured to implement a Coherent Point Microscopy (CPM) approach. The measurement system 10 of the present invention includes a spatially and temporally fully or partially coherent light source 12 (e.g. a laser) and an optical imaging system, generally at 16, for imaging a light response of a sample S to illumination of a point-like light source onto a light sensitive surface 16A (detector plane). A beam/wave $B_{in}$ from the point-like source of monochromatic coherent light is focused onto the sample S under measurements and light beam/wave $B_{out}$, scattered from the sample S is collected and an image thereof is created on a pixel matrix of a light sensitive device (e.g. a CCD).

As shown in the example of FIG. 1, the imaging system 14 includes a collimating lens unit 14A, a beam splitter 14B, an objective lens unit 14C, and a focusing lens (e.g. tube lens) 14D, and a position sensitive detector 16A. In this example, light from the point-like light source 12 is collimated by lens 14A. It should, however be understood, that alternatively, a collimated laser source may be used. The collimated light is focused by the objective 14C onto the beam splitter 14B which directs (reflects) this light beam onto the sample 5, which responds by reflecting/scattering light back towards the objective 14C that focuses the returned light onto the beam splitter 14B which transmits this light to be focused by the tube lens 14D on the position sensitive detector 16. Optionally, the optical system 14 also includes a polarization assembly including a polarizer 18A in the illumination channel (in the optical path of collimated light between the light source and the objective) and a corresponding analyzer 18B in the collection channel (between the objective and the detection plane).

It should be noted that various appropriate implementations of the optical system 14 are possible, provided that the light source, sample's surface and light sensitive surface of the detector are located substantially in conjugate planes, i.e. are located on or close to the conjugate planes. Although in the present non-limiting example the optical system is configured for normal incidence operation, it should be understood that illumination and collection could be done in oblique angles as well, in which case a need for a beam splitter might be eliminated.

As further shown in the figure, the system 10 includes or is connectable to (via wires or wireless signal transmission) a control unit 100. The latter is typically a computing system including inter alia such functional utilities as data input and output utilities 100A and 100D, memory 100B, and a processor utility 100C. The latter is preprogrammed for processing data indicative of the output of the detection unit, i.e. measured data (signal measured on the CCD detector) and determining tone or more sample's characteristics.

Figure 2:
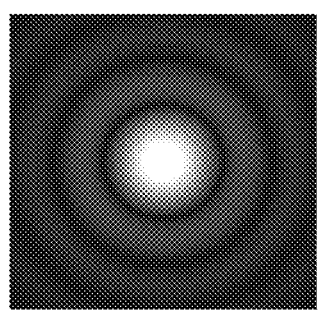
FIG. 2 exemplifies a diffraction limited spot pattern (called an Airy disk) reflected from a perfect mirror.

The novel approach presented in this invention involves imaging the point-like light source scattered from the sample and using the image to characterize the sample. For example, if reflection by the sample does not depend on an incident angle and does not change polarization (the sample's surface operates as a so-called "perfect mirror"), the result of such a measurement is an image of the diffraction-limited light spot. This image is commonly called the system 'point spread function' (PSF), and for an ideal optical system it has the form of an Airy disc. Such an Airy disk pattern/image of a diffraction limited spot reflected from a perfect mirror is shown in FIG. 2.

Conversely, once a nontrivial sample is measured, the image created on the CPM detector may be significantly different from this diffraction-limited spot. We propose to use this change in the spot image as a sensitive probe to the sample's characteristics. As explained below, the reflected pattern is directly related to the scattering matrix. The following is mathematical analysis of the image obtainable by the coherent point microscopy system of the present invention:

In order to describe the complex light field created on the detector of the CPM system of FIG. 1, it is useful to start by defining the sample's scattering matrix by equation (1) above, $\vec{\Omega}_{in/out}$ is the incident/scattered direction and $\vec{P}_{in/out}$ is the incident/scattered polarization.

The complex valued scattering matrix represents the amplitude and phase relation between an incident plane wave with direction $\vec{\Omega}_{in}$ and polarization $\vec{P}_{in}$, and an outgoing plane wave with direction $\vec{\Omega}_{out}$ and polarization $\vec{P}_{out}$. A general incident field can be decomposed into a sum over incident plane waves (through Fourier theorem). Consequently, the scattering matrix can allow calculation of the reflected field for any incident field, and hence completely characterize the scattering properties of the sample.

Common samples in the field of Optical Critical Dimensions (OCD) measurements and thin film characterization are such that no spatial features are resolved optically, i.e. the pattern features are much smaller than the optical wavelength. For the scattering matrices, this means that a corresponding sample is considered a "specular" scatterer where $\vec{\Omega}_{out} = \vec{\Omega}_{in}$ and no diffraction orders are created. When such a sample is illuminated by a coherent monochromatic light source at wavelength λ using a large numerical aperture and is subsequently imaged by an imaging system, the light field on the detector is given by:

$$E_{out}(x,y) = \iiint_{\vec{\Omega} \in NA} E(\vec{\Omega}, \vec{P}_{in}) M_\lambda(\vec{\Omega}, \vec{P}_{in}, \vec{P}_{out}) e^{ik\vec{\Omega}\cdot\vec{r}} d\vec{\Omega} d\vec{P}_{in} d\vec{P}_{out}, \quad (2)$$

where $k=2\pi/\lambda$ is the wavenumber, $E(\vec{\Omega}, \vec{P}_{in})$ is the incident light field and $\vec{r}$ is a spatial coordinate in the detector plane.

It should be noted that in the above expression, the assumption is made that there are no polarizers in the system, so that the signal is the sum over all possible incident and outgoing polarizations.

If the numerical aperture is uniformly illuminated with non-polarized light ($E(\vec{\Omega}, \vec{P}_{in}) = E_0$), and the sample's scattering matrix has equal values for all incident angles and does not affect the polarization, the resulting diffraction pattern on the detector corresponds to the known Airy disk:

$$E(r) = E_0 \left( \frac{2J_1\left(\frac{2\pi NA}{\lambda} r\right)}{\frac{2\pi NA}{\lambda} r} \right). \quad (3)$$

Here, r is the distance from the center of the diffraction-limited point, and $J_1$ is the first Bessel function of the first kind.

In practice, samples are characterized by an angle dependent scattering matrix and often alter polarization upon reflection. The resulting diffraction pattern is more elaborate, and loses the rotational symmetry of the Airy disk. Equation (2) above shows that the measured intensity pattern on the detector in the above-described CPM system, $I(x,y)=|E_{out}(x,y)|^2$, is related to the Fourier transform of the scattering matrix and thus contains information on both its amplitude and phase.

Polarizer(s) is/are preferably added to the CPM setup in order to obtain more information about the sample. The light field is then given by:

$$E_{out}(x,y) = \iiint_{\vec{\Omega} \in NA} \hat{M}_\lambda(\vec{\Omega}, \vec{P}_{in}, \vec{P}_{out}) \vec{E}(\vec{\Omega}, \vec{P}_{in}) e^{ik\vec{\Omega}\cdot\vec{r}} d\vec{\Omega}, \quad (4)$$

where the polarization states of the incident and detected light are specified by the polarizers used. More elaborate measurement schemes, for example additionally incorporating an analyzer, can be similarly treated, implementing well known notation.

Examples for calculated and measured CPM images using the polarizer-analyzer scheme will be described more specifically further below with reference to FIGS. 3 and 4 respectively.

The scattering matrix itself can be calculated for any sample using standard techniques for solving electromagnetic scattering problems (e.g. FDTD, RCWA, FEM, eigenmode expansion etc'). Considering a sample with known geometry, characterized by a set of unknown parameters, such as dimensions, thicknesses and material optical properties (i.e. refractive indices), for any set of values assumed for these parameters, one can calculate the expected (or theoretical) CPM image. Given a measured CPM image, it can be compared to a set of pre-calculated such images. By finding the combination of parameters which produce the best fit between measured and calculated CPM images, one can identify the actual parameters of the measured sample. The model fitting approach is customary for OCD metrology, and is commonly applied for many of the techniques mentioned above.

According to some embodiments of the present invention, CPM measurement setup (exemplified in FIG. 1) could be based on the use of so-called "critical illumination" when a point-like source is directly imaged onto the sample or alternatively by focusing a collimated laser beam on the sample. In such approach, the illumination provides a range of illumination angles onto the sample and coherent interference between different illumination angles. The same situation occurs when an illumination laser beam is out of focus on the sample.

It should be noted that a CPM measurement is not primarily intended to be used as means for microscopy analysis of the sample. Whereas a microscopic image of the sample provides position-dependent information on the local reflectivity of the sample, a CPM image provides a highly nontrivial synthesis of the spatial and angular scattering properties as described above. More generally, other optical testing methods (e.g. Fizeau, Twyman-Green interferometers, Shack-Hartmann) are also commonly used to characterize the spatially-dependent properties (reflected phase, amplitude and polarization) of the sample.

An important attribute of a CPM measurement setup is pristine imaging capabilities for high-coherence light source. This requirement is highly nontrivial: commonly, usage of coherent light introduces strong fringe and speckle effects in the measurement. Several common methods for reduction of these effects are based on the destruction of spatial coherence (e.g. Rotating diffusers). Such solutions would significantly deteriorate the CPM measurement, and as such cannot be used here as-is, and alternative or modified methods must be used. Examples for such methods would be a moving or rotating optical element placed at some location on the optical path which still keeps the imaging constraints between light-source and sample, allowing some small spectral broadening of the light source (which would not lead to significant blurring of the PSF image), allowing some minor spatial incoherence, and\or using high-quality laser-compatible optical elements with limited defects and unwanted reflections.

As a result of the above attributes, a CPM measurement setup is essentially different: the combination of an imaging apparatus in conjunction with coherent light source in critical illumination is currently not accomplished by standard tools.

In order to gain additional information on the sample, it is possible to measure the CPM image using several different wavelengths, possibly from IR down to vacuum UV. This could be done by combining different narrowband light sources or by utilizing a spectrally continuous light source and a set of interchangeable filters or an acousto-optical variable filter. These could be measured one after the other, or simultaneously using spectral separation of the measured CPM image.

One could use a rotating objective turret, so as to allow for the selection of an objective with optimal characteristics in each measurement. For example, different objectives could be used for different wavelengths (allowing high quality measurements over different wavelengths). For example, it is currently a highly complicated task to design and manufacture an objective with high quality performance in both UV and VIS\IR wavelengths. A rotating objective turret can relieve this difficulty altogether. In addition, different illumination schemes can be used, such as angular dark-field, crossed-polarization, Nomarski (DIC), etc. Each such measurement will add independent information on the sample, improving the metrology quality.

More information would be available by using rotatable polarizers and/or retarders in the illumination/detection beam path, as described for example in the above indicated US 2013/308131, which is incorporated herein by reference with respect to this specific example. In addition, measuring the phase of the scattered light by interferometric techniques and/or algorithmic techniques can increase the information contents of the measurement.

In the present invention, the spatial coherence of the light source is crucial because it allows different scattered angles to interfere on the detector and create an interference pattern from which the information can be obtained. An important advantage of CPM is the fact that critically illuminating a sample with coherent light creates a diffraction limited spot on the sample which is the smallest illumination configuration optically possible (i.e. is the optical resolution of the system). In the semiconductor manufacturing field, wafer real-estate is expensive and the ability to achieve metrological measurements on small test sites or even inside the functional areas (dies) is of significant benefit.

In thin film metrology, whereas the reflected field intensity is only weakly affected by the film thickness, the reflected phase is strongly dependant on the film thickness. As described above, the information provided by the CPM based metrology is strongly dependent on the phase characteristics of the reflected electromagnetic field, and as such can provide useful means of measuring the characteristics of thin films. In this application field, use of short wavelength light is of considerable benefit, as the dependence of reflected phase on the film thickness is increased.

As described above, the CPM technique of the present invention provides information on the absolute value of the Fourier transform of the scattering matrix. Since the scattering matrix itself holds complex values, the measured information does not fully specify both its amplitude and phase (see Eq. 1), but rather provides a mathematical relation between them.

It should be noted that it is possible to deduce from such information the separate values of amplitude and phase of the scattering matrix, implementing known information on the measuring optical system. Through such approach, the effective information gained by a CPM measurement is in practice doubled. The method of extracting the complex scattering matrix is based on an algorithmic approach called phase reconstruction, and is frequently used in various fields incorporating optical metrology, most notably astrophysics. Various phase reconstruction algorithms (e.g. the Gerchberg-Saxton (GS), error-reduction, adaptive additive or others) can be utilized for this task. In the GS algorithm for example, the measured intensity is adjoined to an initial guess of a phase function. Then, the complex function is Fourier transformed and constrained with prior knowledge (such as finite NA). The modified function is then inverse Fourier transformed back and compared to the initial measurement. If the reconstructed and initial amplitudes are different, the measured amplitude is adjoined to the reconstructed phase and the cycle starts again. The algorithm continues until the reconstructed amplitude matches the measured amplitude to a predetermined level, and the reconstructed phase is considered the correct one. In the OCD and thin film metrology field, phase retrieval algorithms are especially favorable since an initial guess for the phase could be very accurate due to prior knowledge of the sample. This could enhance the algorithm's convergence speed and reliability.

When combined with phase reconstruction algorithms, the information from a CPM measurement includes the entire information content of a Dome scatterometry measurement, meaning that one can completely derive the result of a Dome measurement from a CPM measurement, whereas the opposite is not true (the information held in a CPM measurement is more comprehensive). In this connection, it should be noted that phase reconstruction is very difficult to apply to dome scatterometry in the same efficient way, since the prior knowledge constraint does not exist.

An additional option for phase reconstruction is to measure both a CPM image and a Dome image. Since the two functions are Fourier connected up to the phase, it is possible similarly to the GS algorithm to start an iterative cycle by the CPM image and an initial guess for the phase and then use the Dome image as the constraint. This could be done by switching the roles of CPM and Dome as well.

As indicated above, the CPM technique of the present invention can be used in optical critical dimension (OCD) metrology. OCD targets are comprised of large arrays (typically several tens of microns in size) of a repeating structure. The result of the OCD metrology is a geometrical and material characterization of the repeating elements, averaged over the multiple (commonly thousands) of separate elements in the array. Such a periodic array reflects light in specific discrete directions, as determined by the grating equation:

$$\theta_{out} = \sin^{-1}\left(\frac{m\lambda}{d} - \sin(\theta_{in})\right). \quad (5)$$

Here, $\lambda$ is the wavelength, d is the grating pitch, $\theta_{in}$ is the incident angle with respect to the normal to the grating, and m is an integer called the diffraction 'order'. The diffracted angles $\theta_{out}$ can have a discrete set of values, as determined by the value of m. Since $\theta_{out}$ cannot exceed $\pi/2$, diffraction occurs only at a limited set of directions. Moreover, for gratings with a small pitch d<$\lambda$, reflection will only occur in the specular direction, i.e. $\theta_{in}=\theta_{out}$. This situation represents the common case in modern OCD applications, which are characterized by very small pitch values.

For simplicity of analysis, we will focus on the case where the target reflects only in the specular direction. This restriction will only serve to simplify the mathematical notation, and extending it to include multiple diffraction orders is straightforward. For specularly reflecting samples, the scattering matrix has the simplified dependence $M_\lambda(\vec{\Omega}_{in}, \vec{P}_{in}, \vec{P}_{out})$, since $\vec{\Omega}_{out}=\vec{\Omega}_{in}$. For notational clarity, we can hence call $\vec{\Omega}\equiv\vec{\Omega}=\vec{\Omega}_{in}$ Following the derivation described above, the CPM image is related to the scattering matrix through $$I(\vec{r})=|\int_{\vec{\Omega}\in NA} E(\vec{\Omega},\vec{P}_{in}) M_\lambda(\vec{\Omega},\vec{P}_{in},\vec{P}_{out}) e^{ik\vec{\Omega}\cdot\vec{r}} d\vec{\Omega}|^2, \quad (6)$$

where $k=2\pi/\lambda$ is the wavenumber, E(Ω) is the incident light-source field and $\vec{r}=(x,y)$ is a spatial coordinate on the detector plane, related to the sample plane by the imaging magnification.

The CPM image is thus in fact the absolute value of the scattering matrix Fourier transform (modified by the illumination and detection characteristics).

Figures 3A, 3B, 4A, 4B:
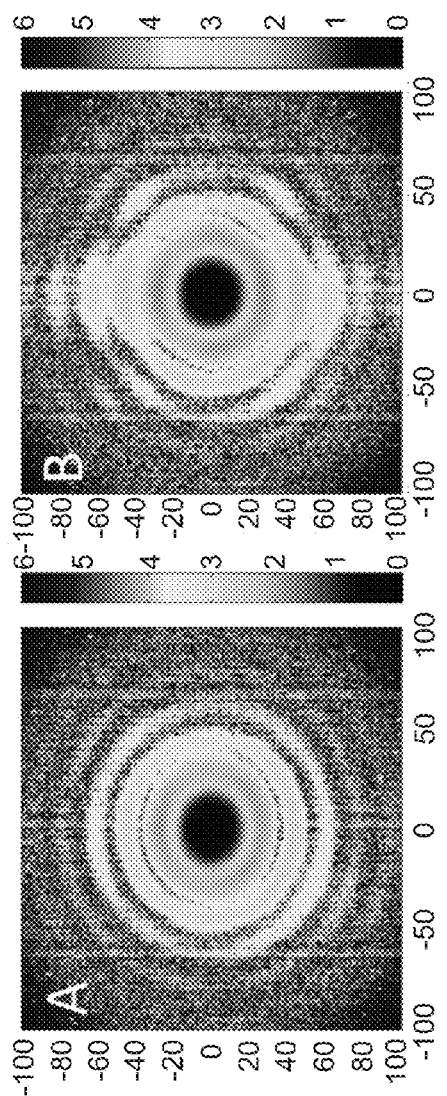
FIGS. 3A and 3B exemplify measured CPM images of a Silicon sample (FIG. 3A) and a grating of 170 nm Silicon oxide lines over Silicon sample (FIG. 3B). The laser wavelength was 633 nm.
FIGS. 4A and 4B exemplify measured cross polarized CPM images of a Silicon sample (FIG. 4A) and an oxide grating over Silicon with a line width of 170 nm (FIG. 4B)

FIGS. 3A and 3B show examples for measured CPM images (log scale) for a Silicon sample (FIG. 3A) and a grating of 170 nm Silicon Oxide lines over Silicon (FIG. 3B). In these examples, the laser wavelength is 633 nm as can be seen in the figure, the CPM image is sensitive to the sample's characteristics.

Comparing the CPM image $I(\vec{r})$ with the result of a dome scatterometry (DS) measurement, a DS image provides the reflected intensity for every reflected direction separately, while a CPM image provides information on the Fourier transform of the scattering matrix, and as such depends on both the amplitude A and the phase ϕ distribution of the scattering matrix. Indeed, for samples which reflect specularly, a DS image measures $|M_\lambda(\vec{\Omega},\vec{P}_{in},\vec{P}_{out})|^2$, which (referring to Eq. 1) is the amplitude A of the scattering matrix in every direction separately. The information from a CPM measurement is thus complementary to that of a DS measurement. As described above, there are advantages to collecting both a CPM and a DS measurement on the same sample.

Multiple CPM images can be obtained, with different configurations applied to the polarizer and analyzer (see FIG. 1), allowing more information on the dependence of $M_\lambda(\vec{\Omega},\vec{P}_{in},\vec{P}_{out})$ on the incident and reflected polarizations. The full characterization of the polarization-dependence of $M_\lambda(\vec{\Omega},\vec{P}_{in},\vec{P}_{out})$ is commonly expressed in the form of the Jones matrix (for samples which do not show depolarization) or the more general Mueller matrix (allowing for depolarization). Standard ellipsometry techniques are used to measure these properties for a large range of wavelengths, but for a single incident direction, implementing 8 independent measurements for characterization of the Jones matrix, or 16 independent measurements for full characterization of the Mueller matrix. Analogously, the same number of CPM measurements can be used to obtain the full Jones or Mueller matrices corresponding to a large range of incident directions (in practice—all directions within the system numerical aperture), and a single wavelength. By obtaining such CPM images using different illumination wavelengths, it is possible to additionally measure the wavelength-dependence of these matrices. Again, these matrices can be compared to a model-based calculation, when a fit between calculation and measurement indicates that the measured sample is characterized by the same geometrical and material parameters as assumed in the calculation.

The required modeling capabilities for calculation of CPM images are different from those of standard reflectometry or ellipsometry. First, CPM metrology implements a relatively small number of wavelengths rather than broadband spectrum, greatly reducing required calculation effort. In contrast, calculation of reflected field in a large-numerical aperture system, as required by CPM, is more demanding than for the small-NA characteristic of reflectometry and ellipsometry.

The algorithms used to compare a CPM measurement and model based calculations can also differ considerably from those used in spectrum-based metrology. Here, image processing tools can be used to selectively highlight important attributes of the CPM image, regions holding significant information and regions\characteristics of the measured image which have strong correlation to parameters of interest in the measured sample.

One specific mode of operation of CPM with noteworthy possible advantage is using crossed-polarization in the illumination and collection channels. In this mode, the polarizer at the illumination channel (16A in FIG. 1) is set at a chosen orientation, whereas the analyzer is set to an orientation perpendicular to it. This way, only reflection components where polarization was rotated are measured, highlighting nontrivial aspects of the reflection. FIGS. 4A and 4B show measured CPM images with cross polarized configuration (log scale) of a silicon sample (FIG. 4A) and an oxide grating over Silicon with a line width of 170 nm (FIG. 4B). In these examples, the illumination source is a laser at a wavelength of 633 nm. In the "perfect mirror" configuration mentioned above, the cross polarized image would look completely dark because the specular reflection will almost prevented from reaching the detector, whereas realistic samples show significant structure. Moreover, the measurement of a Silicon sample is very different from that of a grating sample.

As described above, the CPM image is a result of coherent summation of reflected fields in different directions. Considering use of the CPM approach together a through focus scanning, the effect of defocus adds a relative phase between the different reflected directions before the coherent summation. Since the CPM obtains an absolute value of the coherent sum, the added relative phase changes the measured image in a nontrivial way, further extending the available information.

In principle, when using phase retrieval algorithms to extract both amplitude and phase of the scattering matrix (as discussed above), all relevant information on the scattering matrix can be extracted from a single measurement. However, in such a case the availability of through-focus data can greatly stabilize the phase extraction algorithms, and allow improved numerical convergence and robustness.

One of the important tasks in measurements on patterned structures, in particular semiconductor wafer structures, is the ability to measure parameters of isolated features. Here and in the following the term 'isolated feature' refers to a single feature or a small set of identical features. Leading optical metrology solutions available today, such as spectral reflectometry and spectral ellipsometry, employ a measurement spot of a few tens of microns in diameter. As stated, these measurement spots cover many identical elements, leading to strong reflected signals. Moreover, the measured region is entirely (or at least to a decisive degree) contained inside the test sites, so that the measured reflectivity carries information on the measured target, with no (or minor) effect of the surrounding neighborhood. However, as device dimensions shrink and sensitivity to process details becomes increasingly crucial, the ability to characterize an isolated feature becomes increasingly important. Applying optical metrology to nanometer-scale isolated structures poses a significant challenge, since signal strength will be significantly weaker than that from a periodic array.

CPM technique of the present invention can be applied to an isolated feature with a significant advantage on this aspect. For a diffraction limited spot with large numerical aperture, a spot size has a typical size of less than 1 μm, significantly reducing contributions from the (irrelevant) surroundings of the inspected feature. By using a laser light source, the amount of energy focused onto this small spot can be very large, leading to strong signals and improved SNR. Another possible implementation of the CPM to isolated features is scanning the measurement spot across the isolated feature location. Since the influence of the feature on the measured CPM image is strongly dependent on their relative positioning, such a scanning can be used to significantly increase the amount of independent information on the sample.

The information available from a CPM measurement could be complementary to information from other currently available metrology tools, such as reflectometry, Ellipsometry, CD-SEM and AFM. CPM is especially suitable for such integration, since it can be implemented using a relatively straight-forward measurement arrangement, possibly integrated into a different metrology tool.

There are several possible ways this information can be integrated with other metrology sources:

For example, using CPM with Dome scatterometry (DS) provides for improved characterization of the angular dependence of the scattering matrix. Indeed, as mentioned above, Dome scatterometry measures the absolute value of the scattering matrix vs. incidence angle, while CPM measures the Fourier transform of the scattering matrix. These two measurements can be used to extract the full complex value (amplitude+phase) of the scattering matrix (see Eq. 1). The convergence of phase retrieval algorithms highly depends on the amount of Fourier complementary knowledge such that the Dome/CPM method is favorable. Dome/CPM measurements could be provided for example by at least partially common optical system that is capable to measure CPM and DS simultaneously or in series or by separate measurement systems.

Figure 5:
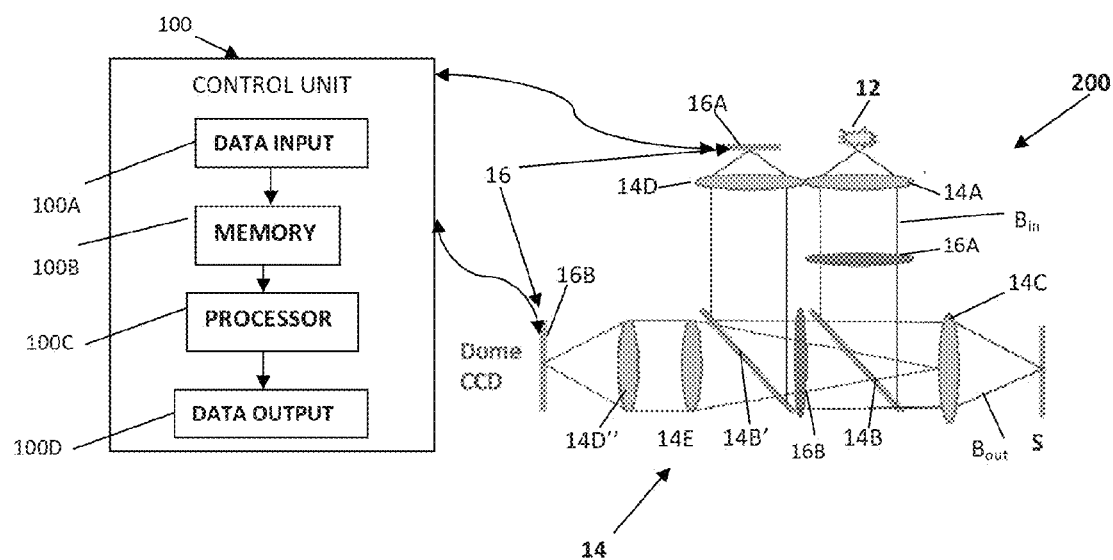
FIG. 5 exemplifies a measurement system of the present invention configured for combining the CPM measurements with those of Dome scatterometry.

In this connection, reference is made to FIG. 5 illustrating schematically an example of a measurement system 200 in including an optical system 14 configured for coherent point microscopy in conjunction with Dome scatterometry. To facilitate illustration and understanding, the same reference numbers are used for identifying structural and functional components of the system in FIGS. 1 and 5. As shown in the figure, the system includes a common point-like source 12 of monochromatic spatially coherent light, an optical system 14 which is formed by the CPM optical setup and additional elements required for concurrent Dome scatterometric measurements, and a detection unit 16 which includes a position sensitive detector 16A (CCD camera) of the CPM setup and a Dome CCD 16B.

Input light $B_{in}$ from the light source 12 is collimated by a tube lens 14A and directed to a polarizer 16A and then to a beam splitter 14B which reflects the polarized light towards the objective 14C which focuses the beam onto a sample S. Light $B_{out}$ returned from the sample S is collected by the objective 14C and then passes through the beam splitter 14B and an analyzer 16B to a second beam splitter 14B' which reflects this light to the CPM detector 16A. The beam splitter 14B' passes a portion of the light to a Bertrand lens 14E followed by a tube lens 14D" which operate together to create an image of the objective back focal plane or any other conjugate or close to conjugate plane on the Dome detector 16B, as illustrated schematically by light rays B'. Measured data from the two detectors (CPM detector 16A, and Dome detector 16B) is collected in parallel or consecutively and then processed and analyzed by the control unit 100, e.g. compared to model calculation as is or used to create a new data set out of the combination of the two collected signals and only then compared to model calculations.

Combining CPM measurements with spectral metrology methods (e.g. reflectometry, scatterometry), provides general improved characterization of the scattering matrix. Such combined measurements enable to obtain a thorough metrology solution for the dependence of the scattering matrix on both wavelength and direction.

In addition, CPM can be used in conjunction with other metrology (e.g. non-optical) techniques, such as CD-SEM, MBIR, CD-SAX etc.

In such measurement schemes, the different inputs from the various metrology tools can be used as basis for comparison with a pre-calculated library as described above. Alternatively or additionally, it is possible to use the information from some metrology channels (e.g. CD-SEM) to establish some unknown dimensions of the sample, and inject these or otherwise "hybridize" them as known parameters in the analysis of the CPM measurement. In addition, the combination of several metrology methods can result in information redundancy which could be used for verification or calibration of the measurement system.

The invention claimed is:

1. A measurement system for measuring one or more parameters of a patterned structure, the system comprising:
   a light source system configured and operable to produce an input beam of at least partially coherent light in spatial and temporal domains;
   a detection system comprising a position sensitive detector configured and operable to receive light and generate measured data indicative of the received light;
   an optical system configured and operable with a numerical aperture selected to focus the input light beam onto a diffraction limited spot on a structure's surface with a range of different illumination angles, collect an output light returned from the illuminated spot, and image the collected output light onto a light sensitive surface of the position sensitive detector, an image of the collected output light being indicative of coherent summation of output light portions of different scattered angles propagating from the structure in different directions; and
   a control unit configured and operable to communicate with the position sensitive detector to receive data corresponding to the measured data indicative of the image of the collected output light, and process the received measured data to determine said one or more parameters of the patterned structure, wherein said processing comprises: determining, from the measured data, a scattering matrix of the patterned structure under measurement, and utilize data indicative of the scattering matrix to determine a relation between the scattering matrix and known data about a point spread function (PSF) of the optical system, said relation being indicative of a reflection pattern of the patterned structure characterizing the one or more parameters of the patterned structure.

2. The measurement system of claim 1, wherein the reflection pattern of the patterned structure is defined by angular distribution of amplitude and phase of the output light.

3. The measurement system of claim 1, wherein the optical system comprises a polarization assembly including a polarizer in an optical path of the input light beam propagating towards the patterned structure, and an analyzer in an optical path of the output light beam propagating from the patterned structure to the detector.

4. The measurement system of claim 1, wherein the optical system is configured to operate in a normal incidence operational mode.

5. The measurement system of claim 1, wherein the optical system is configured to operate in an oblique incidence operational mode.

6. The measurement system of claim 1, wherein the control unit is configured and operable to utilize one or more predetermined models to find a combination of theoretical parameters of a patterned structure producing best fit between the measured data and data calculated by said one or more models, and determine the one or more parameters of the patterned structure.

7. The measurement system of claim 1, wherein the control unit is configured and operable to apply phase retrieval algorithms to the received measured data.

8. The measurement system of claim 1, wherein the control unit is configured and operable to operate the optical system to perform a through focus scanning during measurements, thereby affecting defocus adding a relative phase between different reflected directions before the coherent summation of the output light portions.

9. The measurement system of claim 1, wherein the detection system further comprises a Dome detector, and the optical system is further configured and operable to direct a part of the output light from the patterned structure to the Dome detector, thereby enabling analysis of said measured data and image data of the Dome detector to determine the one or more parameters of the patterned structure.

10. A method for measuring one or more parameters of a patterned structure, the method comprising:
   focusing a light beam of at least partially coherent light in spatial and temporal domains light onto a structure onto a diffraction limited spot on a structure's surface, wherein said focusing is carried out using a relatively large numerical aperture such that the light beam is focused onto the diffraction limited spot with a range of different illumination angles,
   collecting an output light returned from the illuminated diffraction limited spot, and imaging the collected output light onto a light sensitive surface of the position sensitive detector, an image being indicative of coherent summation of output light portions of different scattered angles propagating from the illuminated spot in different directions,
   detecting said output light by the position sensitive detector and generating measured data indicative thereof;
   processing said measured data and determining said one or more parameters of the patterned structure, wherein said processing comprises: determining, from the measured data, a scattering matrix of the patterned structure under measurements, and utilizing data indicative of the scattering matrix and determining a relation between the scattering matrix and known data about a point spread function (PSF) of the measurement system, said relation being indicative of a reflection pattern of the patterned structure characterizing the one or more parameters of the patterned structure.

11. The method of claim 10, wherein the reflection pattern of the patterned structure is defined by angular distribution of amplitude and phase of the output light.

12. The method of claim 10, further comprising polarizing at least one of the input light beam propagating towards the patterned structure, and the output light beam propagating from the patterned structure to the detector.

13. The method of claim 10, comprising utilizing one or more predetermined models for finding a combination of theoretical parameters of a patterned structure producing best fit between the measured data and data calculated by said one or more models, to thereby determine the one or more parameters of the patterned structure.

14. The method of claim 10, further comprising applying phase retrieval algorithms to the received measured data.

15. The method of claim 10, further comprising performing a through focus scanning during measurements, thereby affecting defocus adding a relative phase between different reflected directions before the coherent summation of the output light portions.

* * * * *